United States Patent
Rotem et al.

(10) Patent No.: US 8,337,168 B2
(45) Date of Patent: Dec. 25, 2012

(54) FINGER-TYPE PERISTALTIC PUMP COMPRISING A RIBBED ANVIL

(75) Inventors: Shachar Rotem, M.P. Hefer (IL); Ori Goldor, Amikam (IL)

(73) Assignee: Q-Core Medical Ltd., Petach Tikva (IL)

( * ) Notice: Subject to any disclaimer, the term of this patent is extended or adjusted under 35 U.S.C. 154(b) by 368 days.

(21) Appl. No.: 12/514,310

(22) PCT Filed: Nov. 13, 2007

(86) PCT No.: PCT/IL2007/001398
§ 371 (c)(1),
(2), (4) Date: May 10, 2009

(87) PCT Pub. No.: WO2008/059492
PCT Pub. Date: May 22, 2008

(65) Prior Publication Data
US 2009/0317268 A1    Dec. 24, 2009

(30) Foreign Application Priority Data
Nov. 13, 2006 (IL) .......................... 179231

(51) Int. Cl.
*F04B 43/08* (2006.01)
*F04B 43/12* (2006.01)

(52) U.S. Cl. ...................... 417/53; 417/477.1
(58) Field of Classification Search ......... 417/474–477, 417/53, 477.1, 477.3, 477.9, 478, 479
See application file for complete search history.

(56) References Cited

U.S. PATENT DOCUMENTS
2,056,322 A    10/1936 Hoppe
(Continued)

FOREIGN PATENT DOCUMENTS
DE    10118086 A    7/2002
(Continued)

OTHER PUBLICATIONS

Honeywell Sensing and Control, "FSS1500NSB force sensor", Golden Valley, Minnesota, USA, 1998-2004 http://sccatalog.honeywell.com/imc/printfriendly.asp?FAM=force&PN=FSS150ONSB.

(Continued)

*Primary Examiner* — Anh Mai
*Assistant Examiner* — Elmito Breval
(74) *Attorney, Agent, or Firm* — Vladimir Sherman; Professional Patent Solutions

(57) ABSTRACT

The present invention discloses a finer-type peristaltic infusion pump comprising a ribbed anvil. More specifically, a finger-type peristaltic pump, comprising a plurality of pressing-fingers, infusion-tube, and a passive interfacing mechanism is disclosed. The passive interfacing mechanism comprises of means for accommodating said flexible infusion tube and mounting the tube in a location suitable for the pressing-fingers to apply an approximated perpendicular force on said tube to squeeze it; a ribbed anvil rigidly supporting the tube on opposite side to the pressing fingers when it is pressed by said finger; said anvil comprising a plurality of ribs selected from one or more ribs of a group including a plurality of ribs oriented to face said fingers' tip, a plurality of ribs located in between said fingers, or any combination thereof.

5 Claims, 3 Drawing Sheets

U.S. PATENT DOCUMENTS

| | | | |
|---|---|---|---|
| 2,743,898 A | 5/1956 | King | |
| 3,443,585 A | 5/1969 | Reinicke | |
| 3,982,722 A | 9/1976 | Bernard | |
| 3,982,725 A | 9/1976 | Clark | |
| 4,014,318 A | 3/1977 | Dockum et al. | |
| 4,039,269 A | 8/1977 | Pickering | |
| 4,155,362 A | 5/1979 | Jess | |
| 4,236,880 A | 12/1980 | Archibald | |
| 4,270,532 A | 6/1981 | Franetzki et al. | |
| 4,320,781 A | 3/1982 | Bouvet et al. | |
| 4,450,375 A | 5/1984 | Siegal | |
| 4,489,863 A | 12/1984 | Horchos et al. | |
| 4,682,135 A | 7/1987 | Yamakawa | |
| 4,728,265 A | 3/1988 | Cannon | |
| 4,741,736 A | 5/1988 | Brown | |
| 4,893,991 A | 1/1990 | Heminway et al. | |
| 4,978,335 A | 12/1990 | Arthur, III | |
| 5,096,385 A | 3/1992 | Georgi et al. | |
| 5,103,211 A | 4/1992 | Daoud et al. | |
| 5,152,680 A | 10/1992 | Okada | |
| 5,165,874 A | 11/1992 | Sancoff et al. | |
| 5,213,483 A | 5/1993 | Flaherty et al. | |
| 5,222,946 A | 6/1993 | Kamen | |
| 5,257,978 A | 11/1993 | Haber et al. | |
| 5,290,158 A | 3/1994 | Okada | |
| 5,395,320 A | 3/1995 | Padda et al. | |
| 5,429,485 A | 7/1995 | Dodge | |
| 5,499,969 A | 3/1996 | Beuchat et al. | |
| 5,509,439 A | 4/1996 | Tantardini | |
| 5,527,295 A | 6/1996 | Wing | |
| 5,575,309 A | 11/1996 | Connell | |
| 5,577,891 A | 11/1996 | Loughnane et al. | |
| 5,593,134 A | 1/1997 | Steber et al. | |
| 5,658,252 A | 8/1997 | Johnson | |
| 5,683,233 A | 11/1997 | Moubayed et al. | |
| 5,782,805 A | 7/1998 | Meinzer et al. | |
| 5,807,322 A | 9/1998 | Lindsey et al. | |
| 5,896,076 A | 4/1999 | Van Namen | |
| 5,996,964 A | 12/1999 | Ben-Shalom | |
| 6,095,189 A | 8/2000 | Ben-Shalom | |
| 6,164,921 A | 12/2000 | Moubayed et al. | |
| 6,165,874 A | 12/2000 | Powell et al. | |
| 6,203,296 B1 | 3/2001 | Ray et al. | |
| 6,213,739 B1 * | 4/2001 | Phallen et al. | 417/478 |
| 6,261,262 B1 | 7/2001 | Briggs et al. | |
| 6,339,410 B1 | 1/2002 | Milner et al. | |
| 6,371,732 B1 | 4/2002 | Moubayed et al. | |
| 6,450,773 B1 | 9/2002 | Upton | |
| 6,537,244 B2 | 3/2003 | Paukovits et al. | |
| 6,692,241 B2 | 2/2004 | Watanabe et al. | |
| 6,733,476 B2 | 5/2004 | Christenson et al. | |
| 7,018,361 B2 | 3/2006 | Gillespie, Jr. et al. | |
| 7,022,075 B2 | 4/2006 | Grunwald et al. | |
| 7,122,026 B2 | 10/2006 | Rogers et al. | |
| 7,163,385 B2 | 1/2007 | Gharib et al. | |
| 2002/0156402 A1 | 10/2002 | Woog et al. | |
| 2002/0165503 A1 | 11/2002 | Morris et al. | |
| 2003/0040700 A1 | 2/2003 | Hickle et al. | |
| 2003/0182586 A1 | 9/2003 | Numano | |
| 2004/0181314 A1 | 9/2004 | Zaleski | |
| 2004/0191112 A1 | 9/2004 | Hill et al. | |
| 2005/0088409 A1 | 4/2005 | Van Berkel | |
| 2006/0051218 A1 | 3/2006 | Harttig | |
| 2006/0083644 A1 * | 4/2006 | Zumbrum et al. | 417/476 |
| 2007/0269324 A1 | 11/2007 | Goldor et al. | |
| 2008/0095649 A1 | 4/2008 | Ben-Shalom et al. | |

FOREIGN PATENT DOCUMENTS

| | | | |
|---|---|---|---|
| EP | 0215249 A1 | 3/1987 | |
| EP | 0225158 A2 | 6/1987 | |
| FR | 2632529 A | 12/1989 | |
| JP | 60043188 A | 3/1985 | |
| JP | 6-169992 A | 6/1994 | |
| JP | 2002-57738 A | 2/2002 | |
| JP | 2004141418 A | 5/2004 | |
| WO | 9116933 A1 | 11/1991 | |
| WO | 03027503 A1 | 4/2003 | |
| WO | 2008059493 A2 | 5/2008 | |
| WO | 2008059494 A2 | 5/2008 | |
| WO | 2008059495 A2 | 5/2008 | |
| WO | 2008059496 A2 | 5/2008 | |
| WO | 2008059498 A2 | 5/2008 | |
| WO | 2008059499 A2 | 5/2008 | |
| WO | 2008130644 A1 | 10/2008 | |

OTHER PUBLICATIONS

U.S. Appl. No. 12/644,027 Official Action dated Apr. 28, 2011.
U.S. Appl. No. 11/791,599 Official Action dated Mar. 31, 2011.
European Patent Application # 10192477.7 Search Report dated May 10, 2011.
U.S. Appl. No. 10/535,103 Official Action dated Feb. 2, 2009.
International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
International Application PCT/IL2003/000947 Search Report dated Mar. 3, 2004.
Chinese Patent Application No. 200580045471.3 "Finger-type peristaltic pump" Official Action dated Jul. 18, 2008.
U.S. Appl. No. 09/125,438 Official dated Jul. 15, 1999.
U.S. Appl. No. 09/125,438 Official dated May 3, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
Chinese Patent Application No. 200780041966.8 Official Action dated Jul. 13, 2010.
U.S. Appl. No. 11/791,599 Official dated Aug. 19, 2010.
U.S. Appl. No. 12/514,311 Official dated Sep. 16, 2010.
U.S. Appl. No. 12/464,202 Official Action dated Oct. 3, 2011.
U.S. Appl. No. 12/463,399 Official Action dated Jul. 21, 2011.

* cited by examiner

FINGER-TYPE PERISTALTIC PUMP COMPRISING A RIBBED ANVIL

FIELD OF THE INVENTION

The present invention generally relates to a finer-type peristaltic infusion pump comprising a ribbed anvil rigidly accepting a flexible infusion tube when it is pressed by a pressing-finger

BACKGROUND OF THE INVENTION

This invention relates to a design using ribs on the pumping substrate of a peristaltic pump. At present peristaltic pumps find use in medical settings to add nutrients to blood, to force blood through filters to clean it as in dialysis, or to move blood through the body and lungs during open heart surgery. They are advantageous in these situations since the pump elements do not contact the pumped fluid, eliminating any possibility of contamination. Additionally the pumping action is gentle enough that blood cells are not damaged. Further uses include pumping aggressive chemicals, high solids slurries and other materials where isolation of the product from the environment, and the environment from the product, are critical. As the operation of such a pump can be critical for life support, they are generally provided with battery back up. The efficiency of the device thus becomes an important parameter since the length of time it can remain in operation while on battery power is limited by its efficiency.

SUMMARY OF THE INVENTION

It is thus the object of the present invention to provide a finer-type peristaltic pump (DDS) comprising a plurality of pressing-fingers, infusion-tube, and a passive interface mechanism; wherein this passive interface mechanism comprising (a) a means for accommodating said flexible infusion tube and mounting the same in a location suitable for said pressing-fingers to apply an approximated tangential force on said tube to squeeze it; (b) a ribbed anvil rigidly accepting said flexible tube when it is pressed by said finger; and further wherein said anvil comprising one or more of the following (i) a plurality of ribs facing said fingers' tip, (ii) a plurality of ribs located in between said fingers, or (iii) any combination thereof.

Another object is to provide a DDS as defined above, wherein one or more of said ribs is of a different height as compared with others ribs (reference ribs), so as the squeezed volume of the infused fluid per pumping cycle provided by said one or more ribs is either bigger or smaller height as compared with squeezed volume provided by said reference ribs.

Another object is to provide a DDS as defined above, wherein one or more of said ribs is of a different width as compared with others ribs (reference ribs), so as less pressing force is required by a given finger for shutting off said infusion tube against narrower ribs as compared with reference ribs, and vice versa, more pressing force is required by a given finger for shutting off said infusion tube against wider ribs as compared with reference ribs.

Another object is to provide a DDS as defined above, especially adapted to provide optimization means for calibrating each finger's force requirements per single pumping cycle by widening or narrowing adjacent rib's width.

Another object is to provide a DDS as defined above, wherein one or more of said ribs is of a different specifications: namely width and/or profile characteristics as compared with others ribs (reference ribs), in the manner that less pressing force is required by a given finger for shutting off said infusion tube against said ribs as compared with said reference ribs, so as minimized tube's degradation is provided due to continuous shutting off of the flexible tube by said fingers pressing tips.

Another object is to provide a method of obtaining a predetermined flow capacity, comprising of obtaining a DDS as defined in any of the above; and adjusting the specifications one or more of said ribs, namely altering its width and/or profile characteristics, hence accepting a respectively wide range of infusion-tubes types, flexibility, conditions and diameters, with no requirement of controlling pump's pumping parameters

BRIEF DESCRIPTION OF THE FIGURES

In order to understand the invention and to see how it may be implemented in practice, a plurality of preferred embodiments will now be described, by way of non-limiting example only, with reference to the accompanying drawing, in which FIG. 1 schematically illustrating an out-of-scale and simplified lateral cross-section of tube pressing mechanism in a finger-type infusion-pump according to one embodiment of the present invention.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a finer-type peristaltic pump comprising a ribbed anvil rigidly accepting a flexible infusion tube when it is pressed by a pressing-finger.

The term 'plurality' refers hereinafter to any integer number equal or higher 1, e.g., 2 to 10, especially 2 to 4.

The present invention pertains to finger-type peristaltic pump (DDS) that utilizes a passive mechanical interface adapted to incorporate a set of infusion tubing with a pumping mechanism and various sensors, wherein the back portion of the mechanical interface is provided as an anvil accepting those M pressing fingers.

The term passive interface relates to a mechanical interface of the set tubing to the DDS that has no moving parts or static members being an integral part of the aforesaid pumping mechanism of sensors thereof, e.g., pistols, hinges, cams, wheels, sealing membranes, gaskets etc. A plurality of N ribs is located inside said back-portion of the interface. A portion of the ribs ($n_1$) is located below the fingers tips, and a portion ($n_2$) is located in between those fingers. N and M are any integer numbers, wherein $n_1$ is either equal or different then $n_2$. It is acknowledged in this respect that according to one possible embodiment of the present invention, no ribs are located under the fingers. The ribs provide useful means for calibrating the flowing volume in said tube in each pumping cycle. The ribs further provide useful means for an individual calibration of the force requires by each of the pressing fingers to complete shutoff of the infusion tube. The ribs further allow optimization of the energy consumes to shutoff the tube and the energy requires allowing fluids flow in said tube. The ribs also provide useful means for minimizing degradation of the infusion tube, especially by optimizing the surfaces of the finger tips continuously pressing the tube. Moreover, the present invention also provides useful means for energy optimization. Lastly, the ribs facilitate the immobilization the infusion tube by mechanical interface of the pressing fingers, e.g., to approach a relatively wide range of tubes (diameter, elasticity, regulatory of the surface etc) so as a constant volume of fluid is pumped per a given pumping cycle.

Figure 1:
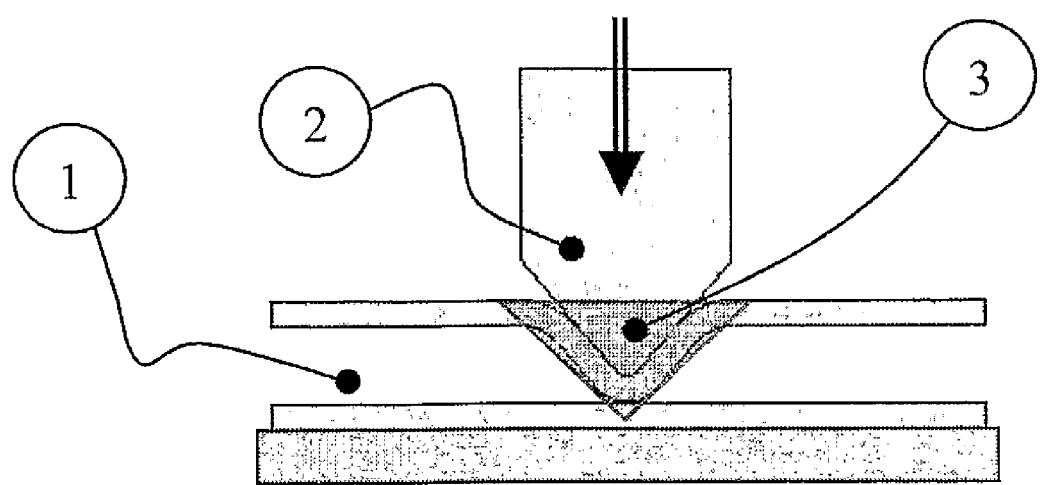
Figure 2:
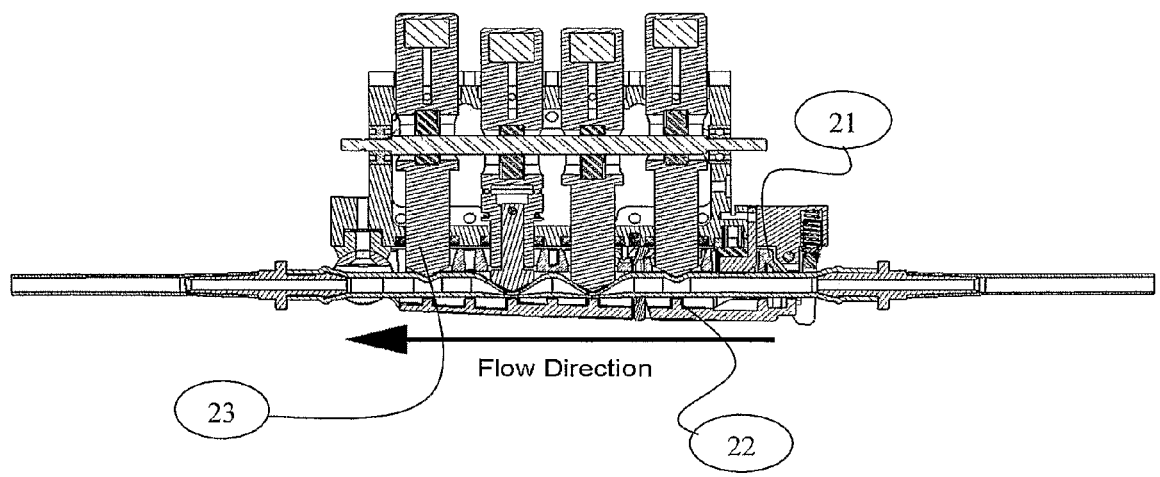
FIG. 2 schematically illustrating a detailed lateral cross-section of the pressing fingers and infusion tube in an infusion-pump according to one embodiment of the present invention; and, FIG. 3 schematically illustrating two out-of-scale and simplified lateral cross-sections of a pressing mechanism as defined above; higher view comprises of a non-ribbed anvil (prior art), and lower view comprises ribbed-anvil according to one embodiment of the present invention.

Controlling the volume of fluid is pumped per a given pumping cycle: Reference is now made to FIGS. 1 and 2, wherein FIG. 1 schematically illustrates an out of scale lateral cross section of an infusion tube (1), wherein a perpendicular peristaltic finger (2) is reversibly mounted and pressing the same so as a measurable volume of fluid (3) is squeezed due to the tube's shutoff. Hence, squeezed volume (3) is regulated by the pressing finger (2). Some of the fluid (3) is pressed upstream and some is pressed downstream. The volume of upstream pressed fluid (against an adjacent tube's shutoff provided by a neighboring pressing finger) is dependent on the flexibility of the tube and on the existence of rigid envelops accommodating the tube and restricting its inflation. It is acknowledged in this respect that in an extreme case, a very flexible tube is utilized; the diameter of this flexible tube is not restricted by a rigid envelope, so as by providing a high pressure zone downstream to the press, most of the fluid is pressed backwards and not forwards. It is hence in the scope of the present invention wherein regulation of geometry of the mechanical interface of a finger-type peristaltic pumps, tube's inflation can be regulate and backwards flow of fluid at each pumping cycle can be avoided. As a result, one can optimize the volume of fluid to be pump per a given pumping cycle and minimize losses obtained by upstream flow of the fluid.

FIG. 2 schematically illustrates an out-of-scale lateral cross section of a finger-type peristaltic pump that comprises a plurality of 4 fingers being rotatably mounted perpendicular to an infusion tube. A mechanical interface (21) avoids inflation of the tube along the pumping and provides exact regulation of the volume of the squeezed fluid at each pumping cycle. By determining the measurements of the ribs (22) under the pressing fingers, an exact calibration of the force require to shutoff the tube by each finger (23) is provided.

Optimization of Energy Requires to Shutoff the Infusion Tube vs Energy Requires to Facilitate a Fluid Flow Thorough This Tube The pumping fingers are adapted to apply an approximately perpendicular force on the flexible infusion tube to squeeze it, so as one of its walls will bend and touch the opposite wall and fluids flow will shutoff. In theory a continues contact line between the tube walls will produce a complete shutoff, however grater force is needed to produces a pressure—on the tube walls—high enough to overcome tube's surface irregularities. It is acknowledged that smaller pressing area in the aforesaid tube's shutoff location requires less force. Upper zoomed-in scheme presents a case of the prior art whereat pressing-forces are spread upon the flexible tube, more area is to be squeezed and hence stronger forces are to be applied; wherein lower zoomed-in scheme presents a case according to one embodiment of the present invention wherein pressing forces are focused towards the rib and less force is required for complete shut off of the infusion tube.

Figure 3:
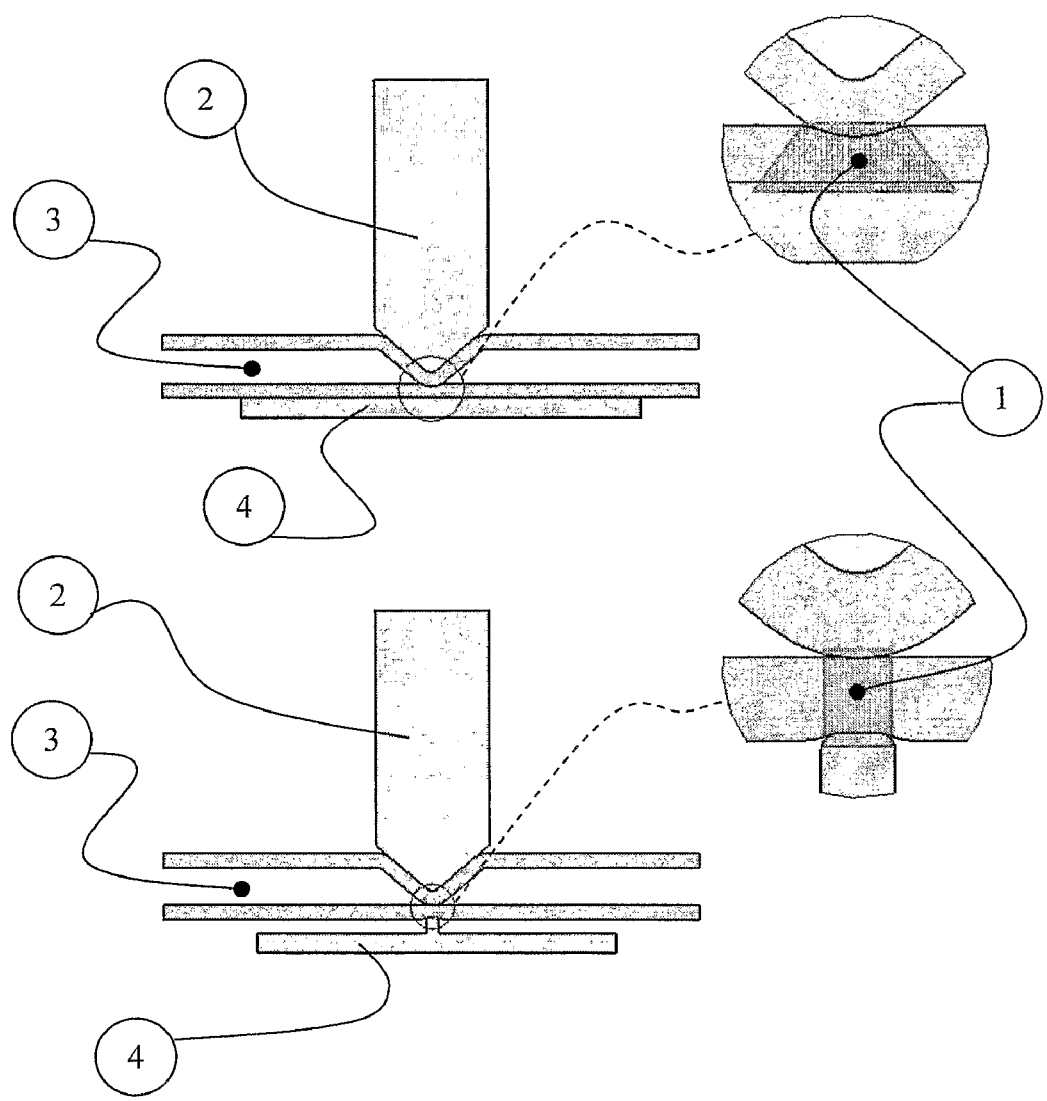

Reference is now made to FIG. 3, schematically illustrating out-of-scale lateral cross sections of pressing mechanism of finger-type peristaltic pumps that comprise a pressing-finger (2) which presses tube (3) towards an anvil (4) at a given pressing area (1). Higher illustrations present a plain anvil (4) (See also wide pressing area at the zooming view on the right); wherein lower illustrations present a ribbed anvil with respectively narrow pressing area at the zooming view on the right.

It is in the scope of the invention wherein the capacity of the flow can be calibrated, e.g., by adjusting the width or other proportions of one or more ribs. Similarly, the force which is required to provide an optimal flow capacity can be calibrated and adjusted. The proportions of length and width of ribs under the pressing fingers, rib's profile and cross sections, as well as other dimensions of the rids in the passive interface mechanism, allow the optimization of capacity to flow ratio. The height of the ribs under the pressing fingers provides for calibration of the sealing properties of eh mechanism. A method of calibrating the fluid's flow capacity is also disclosed, and comprised of steps of adjusting the proportions of the ribs under the pressing fingers as defined above.

The invention claimed is:

1. A finger-type peristaltic pump (DDS), comprising a plurality of pressing-fingers, a tube, and a passive interfacing mechanism; wherein said passive interfacing mechanism comprises (a) a channel for accommodating said tube and mounting said tube in a location suitable for said pressing-fingers to apply substantially perpendicular force on said tube; (b) a ribbed anvil rigidly supporting said tube on opposite side to said pressing fingers, wherein said anvil includes at least one fixed protruding rib located at a defined position relative to at least one of said fingers; and wherein by changing the heights of one or more of said ribs it is possible to calibrate the squeezed volume of the infused fluid per pumping cycle, said squeezed volume is defined by ribs of a nominal height, so as the ratio between squeezed volume per revolution and the speed of the pumping mechanism can be calibrated.

2. The finger-type peristaltic pump according to claim 1, wherein one or more of said ribs is of a different width as compared with others ribs (reference ribs), so as less pressing force is required by a given finger for shutting off said infusion-tube against narrower ribs, as compared with reference ribs of wider width, and vice versa, more force is required for pressing said tube by a given finger against wider ribs as compared with reference narrower ribs.

3. The finger-type peristaltic pump according to claim 1, wherein one or more of said ribs is of a different width as compared with others ribs (reference ribs), so as squeezed volume of the infused fluid per pumping cycle can be calibrated.

4. The peristaltic pump of claim 1, wherein said anvil includes one or more fixed protruding ribs between said pressing fingers to achieve a predetermined flow rate through the tube.

5. The peristaltic pump of claim 1, wherein said anvil includes one or more fixed protruding ribs substantially across from one or more of said fingers tips to decrease the force required by pressing fingers to close the tube.

* * * * *